United States Patent [19]

Haruna et al.

[11] Patent Number: 4,999,393
[45] Date of Patent: Mar. 12, 1991

[54] PHOSPHONITE COMPOUND AND SYNTHETIC RESIN COMPOSITION

[75] Inventors: Tohru Haruna, Saitama; Kazunori Nishikawa, Chiba, both of Japan

[73] Assignee: Adeka Argus Chemical Co., Ltd., Tokyo, Japan

[21] Appl. No.: 306,921

[22] Filed: Feb. 6, 1989

[30] Foreign Application Priority Data

Feb. 10, 1988 [JP] Japan .................. 63-29162

[51] Int. Cl.⁵ ................ C08K 5/53; C07F 9/02
[52] U.S. Cl. ................ 524/126; 558/83; 558/85
[58] Field of Search ............ 558/83, 85; 524/119, 524/126

[56] References Cited

U.S. PATENT DOCUMENTS 3,297,631  1/1967  Bown et al. ............ 558/83
4,143,028  3/1979  Spivack ................ 558/83
4,481,317 11/1984  Nakahara et al. ....... 524/119

OTHER PUBLICATIONS

In re Payne, 203 USPQ, 1979, pp. 245-258.

*Primary Examiner*—Jose G. Dees
*Assistant Examiner*—Deboroh D. Carr
*Attorney, Agent, or Firm*—Barnes, Kisselle, Raisch, Choate, Whittemore & Hulbert

[57] ABSTRACT

A cyclic phosphonite compound having the following formula (I) is disclosed and useful as a stabilizer for a synthetic resin.

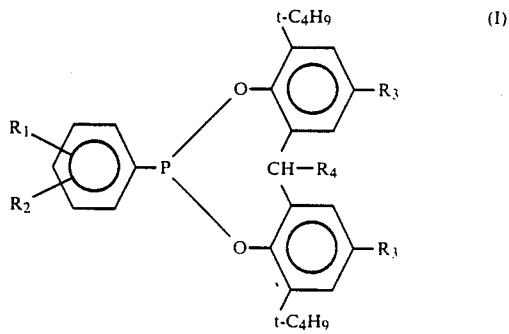

in which R1 is an alkyl, phenyl or an alkylphenyl, R2 is hydrogen or an alkyl, R3 is an alkyl, R4 is hydrogen or methyl and R1 and R2 may form an alkylene by linking each other.

10 Claims, No Drawings

PHOSPHONITE COMPOUND AND SYNTHETIC RESIN COMPOSITION

This invention relates to the compositions of stabilized synthetic resins and more specifically to the compositions of synthetic resins made more stable and resistant to the deterioration by heat and light, by adding particular cyclic phosphonite compounds.

It is well known that polyethylene, polypropyrene, ABS resins, polyvinyl chloride resins and other similar synthetic resins are deteriorated, colored or lowered in their mechanical strength by the action of heat and light, thus becoming less endurable to a long-term use.

In order to prevent such deterioration, a plenty of additives have so far been used either independently or in combination. It is known that among these additives, the phosphonite compound can improve the heat resistance and is of relatively great effectiveness in controlling the coloration. For example, U.S. Pat. No. 3,297,631 proposes, as such an additive, 2,2′-methylene-bis (dialkylphenyl) benzenephosphonite compound; Japanese Provisional Patent Publication No. 8772-1972 proposes tetra (dialkylphenyl) biphenylene diphosphonite compound, Japanese Provisional Patent Publication No. 90187-1979, tetra-alkyl biphenyl benzenephosphonite compound, and Japanese Provisional Patent Publication No. 108239-1983, bis ((2,2′- methylene-bis (dialkylphenyl))) biphenylene diphosphonite compound.

The stabilizing effect of such compounds as above remains however still insufficient and more effective compounds have been looked for.

As the results of our researches to remove the above disadvantages, we have eventually found that by adding a compound as represented by the following general formula (I) the thermal and light resistance of synthetic resins can be outstandingly be improved.

This invention provides a cyclic phosphonite compound having the following formula (I):

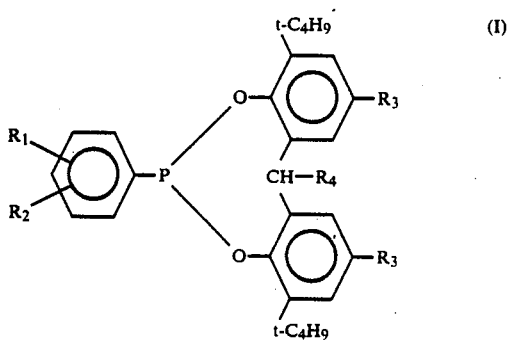

in which R1 is an alkyl, phenyl or an alkylphenyl, R2 is hydrogen or an alkyl, R3 is an alkyl, R4 is hydrogen or methyl and R1 and R2 may form an alkylene by linking each other.

It is useful as a stabilizer for a synthetic resin.

In the formula (I), it is preferable that R1 is an alkyl having 1 to 18 carbon atoms, R2 is hydrogen, R3 is an alkyl having 1 to 18 carbon atoms and R4 is hydrogen. It is more preferable that R1 is methyl and R3 is an alkyl having 1 to 4 carbon atoms.

The invention further provides a synthetic resin composition which comprises 100 parts by weight of a synthetic resin and 0.01 to 10 parts by weight of the compound as defined above.

The composition may further comprise 0.001 to 5 parts by weight of an anti-oxidant of the phenol type such as 3,5-dialkyl-4-hydroxyphenyl-propionic acid ester, tetrakis(methylene-beta-(3,5-di-tertiary-butyl-4-hydroxyphenyl)propionate)methane, stearyl-beta-(3,5-di-tertiary-butyl-4-hydroxyphenyl)propionate, tris(alkylated-hydroxybenzyl)isocyanurate and 3,5-tris(3,5-di-tertiary-4-hydroxybenzyl)isocyanurate.

It is preferable that the resin is a polyolefin.

In the above formula (I), we can enumerate as the alkyl group to be represented by $R_1$, $R_2$ or $R_3$, methyl, ethyl, propyl, isopropyl, butyl, sec-butyl, tert-butyl, isobutyl, amyl, tert-amyl, hexyl, heptyl, octyl, isooctyl, 2-ethylhexyl, nonyl, isononyl, tert-nonyl, decyl, isodecyl, dodecyl, tetradecyl, hexadecyl, octadecyl and so forth; as the alkylphenyl represented by $R_1$, the phenyl group substituted by the above alkyl group; and as the alkylene group to be formed by bonding of $R_1$ with $R_2$, we can enumerate trimethylene, tetramethylene, pentamethylene and so forth.

Such compound as represented by the above formula (I) which is used in this invention, can be easily produced by allowing 2,2′-alkylidene-bis (4-alkyl-6-tert-butylphenol) to react, by conventional procedure, with substituted phenyl dichlorophosphine compound, represented by a formula:

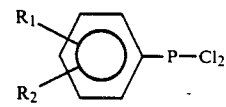

This substituted phenyl dichlorophosphine compound can be obtained by allowing, for example, phosphorous trichloride to react with substituted benzene compound represented by the following formula:

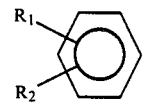

As the 2,2′-alkylidene-bis (dialkylphenol) to be used as a substance for producing the phosphonite compound by this invention, we may enumerate: 2,2′-methylene-bis (4-ethyl-6-tert-butylphenol), 2,2′-methylene-bis (4,6-di-tert-butylphenol), 2,2′-ethylidene-bis (4-methyl-6-tert-butylphenol), 2,2′-ethylidene-bis (4,6-di-tert-butylphenol), 2,2′-ethylidene-bis (4-sec-butyl-6-tert-butylphenol) and others.

In consequence we may enumerate such compounds as shown under Table 1 below, as the compounds indicated by the above general formula (I):

TABLE 1

No. 1

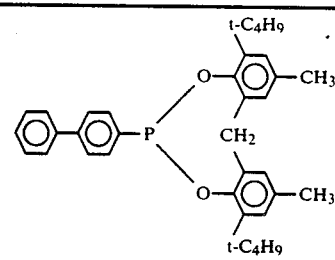

TABLE 1-continued

No. 2
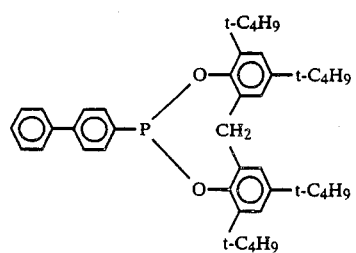

No. 3
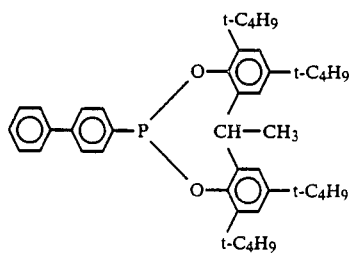

No. 4
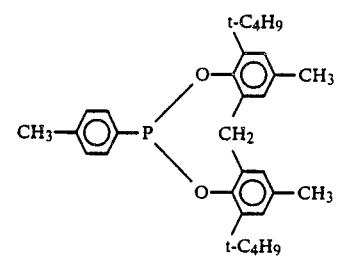

No. 5
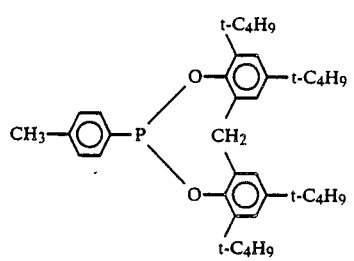

No. 6
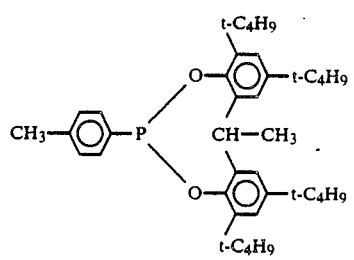

No. 7
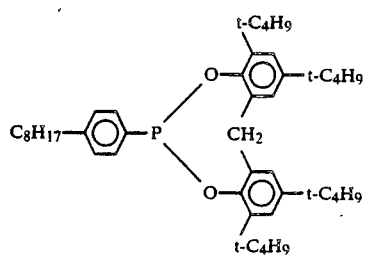

TABLE 1-continued

No. 8
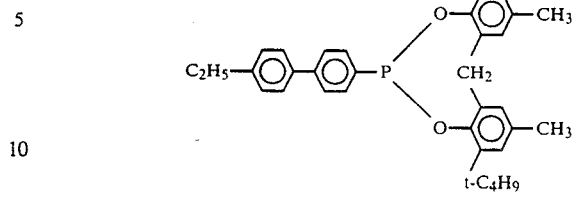

No. 9
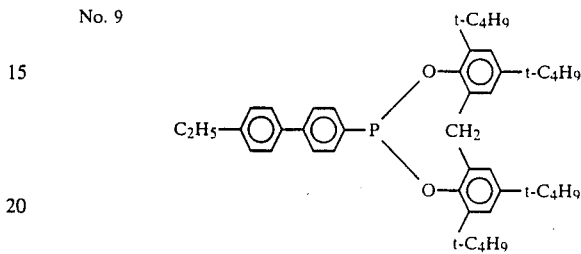

No. 10
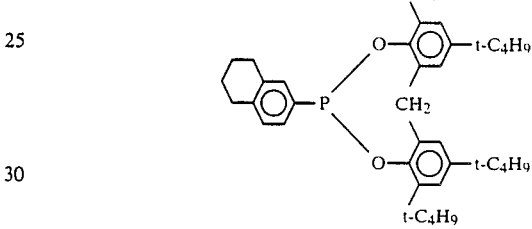

No. 11
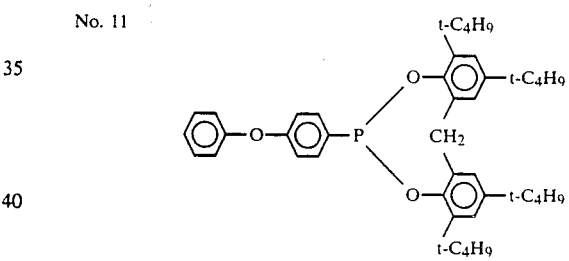

This invention will be understood more easily with reference to the following examples of syntheses of the above compounds; however these examples are intended to illustrate the invention and are not to be construed to limit the scope of the invention.

EXAMPLE OF SYNTHESIS 1 (SYNTHESIS OF THE COMPOUND NO. 1 AS UNDER TABLE 1)

6.4 g of the 4-biphenyl dichlorophosphine synthesized from biphenyl and phosphorous trichloride through conventional procedure, 6.4 g of 2,2'-methylene bis (4,6-di-tert-butylphenol), 0.1 g of triethylamine and 50 ml of xylene were stirred at 130° C. for 5 hours. After neutralization with triethylamine, hydrochloride of the triethylamine produced was filtered. The filtrate was then cooled to deposit the crystals. After filtration washing was made using methanol a product of white powder with melting point of 250° to 260° C. could be obtained. $H^1$-NMR (60 MHz, with TMS as standard) measured in heavy chloroform resulted in as below, which allowed us to confirm our desired object:

| Delta Value: | 1.3 to 1.4: 36 H, ss tert-butyl group, |
| | 3.3 to 4.7: 2 H, dd methylene |

| -continued |
|---|
| 7.2 to 8.2: 13 H, m aromatic hydrogen |

EXAMPLE OF SYNTHESIS 2 (SYNTHESIS OF THE COMPOUND NO. 5 AS UNDER TABLE 1)

We could obtain a product of white powder with 240° to 250° C. of melting point in a same way as in Example 1 hereabove, except that we used in this case 3.9 g of 4-methylphenyl dichlorphosphine and 8.5 g of 2,2'- methylene-bis (4,6-di-tert-butylphenol).

The result of the measurement of H$^1$-NMR (60 MHz, with TMS as standard) in the heavy chloroform was as below, which allowed us to confirm our desired object:

| Delta Value: | 1.2 to 1.3: 36 H, ss tert-butyl group |
|---|---|
| | 2.3 to 2.4: 3 H, s methyl group |
| | 3.2 to 4.4: 2 H, dd methylene |
| | 7.0 to 8.0: 8 H, m aromatic hydrogen |

Loads of these compounds to the synthetic resin of 100 parts in weight are 0.001 to 10 parts by weight, and more preferably 0.01 to 3 parts by weight.

Some examples of the synthetic resins to be stabilized by this invention are: such polyolefins as polyethylene, polypropylene, ploybutene, poly-3-methybutene and other α-olefin polymers, or ethylene-vinyl acetate copolymer, ethylene-propylene copolymer as well as the co-polymers thereof; such synthetic resins including halogens as polyvinyl chloride, polyvinyl bromide, polyvinyl fluoride, polyvinylidene chloride, chlorinated polyethylene, chlorinated polypropylene, polyvinylidene fluoride, brominated polyethylene, chlorinated rubber, vinyl chloride-vinyl acetate copolymer, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride terpolymer, vinyl chloride-styrene-acrylonitrile copolymer, vinyl chloride-butadiene copolymer, vinyl chloride-chlorinated propylene copolymer, vinyl chloride-vinylidene chloride-vinyl acetate terpolymer, vinyl chloride-acrylic ester copolymer, vinyl chloride-maleate ester copolymer, vinyl chloride-metacrylate ester copolymer, vinyl chloride-acrylonitrile copolymer; copolymers of petroleum resin, coumarone resin, polystyrene, polyvinyl acetate, acrylic resin, polyacrylonitrile, and styrene with other monomers (for example, maleic anhydride, butadiene, acrylonitrile); ABS resins, so-called high heat-resistant ABS resin with part or all of styrene component of ABS resin substituted by α-methylstyrene, so-called high heat resistant ABS resin in which maleimides are copolymerized as a component of ABS resin; such methacrylate resins as acrylic ester-butadiene-styrene copolymer, polymethyl methacrylate; and polyvinyl alcohol, polyvinyl formal, polyvinyl butyral, linear polyester, polyphenylene oxide, polyamide, polycarbonate, polyacetal, polyurethane, cellulosic resins, or phenolic resins, urea resins, melamine resins, epoxy resins, unsaturated polyester resins, silicon resins.

Further they may be such rubbers as isoprene rubber, butadiene rubber, acrylonitrile-butadiene copolymer rubber, styrene-butadiene copolymer rubber or blends of these resins.

Adding known phenolic antioxidants to the composition by this invention will further improve the oxidative stability thereof. As such phenolic antioxidants we may enumerate: 2,6-di-tert-butyl-p-cresol, 2,6-diphenyl-4-octadecyl oxyphenol, stearyl (3,5-di-tert-butyl-4-hydroxyphenyl)-propionate, distearyl (3,5-di-tert-butyl-4-hydroxybenzyl) phosphonate, thiodiethyleneglycolbis (((3,5-di-tert-butyl-4-hydroxyphenyl) propionate)), 4,4'-thiobis (6-tert-butyl-m-cresol) 2-octylthio-4,6-di (3', 5'-dihydroxyl phenoxy)-s-triazine, 2,2'-methylenebis (4-methyl-6-tert-butylphenol), 2,2'-methylenebis (4-ethyl-6-tert-butylphenol), bis ((3,3-bis (4'-hydroxy-3'-tert-butylphenol) butylic acid)), glycol ester, 4,4'-butylidenebis (6-tert-butyl-m-cresol), 2,2'-ethylenebis (4,6-di-tert-butylphenol), 2,2'-ethylidenebis (4-sec-butyl-6-tert-butylphenol) 1,1,3-tris (2'-methyl-4'-hydroxy-5'-tert-butylphenyl) butane, bis ((2-tert-butyl-4-methyl-6-(2'-hydroxy-3'-tert-butyl-5'-methylbenzene) phenyl)) terephthalate, 1,3,5-tris (2', 6'-dimethyl-3'hydroxy-4'-tert-butylbenzyl) isocyanurate, 1,3,5-tris (3', 5'-di-tert-butyl-4'-hydroxybenzyl) isocyanurate, 1,3,5-tris (3', 5'-di-tert-butyle-4'-hydroxybenzyl)-2,4,6-trimethylbenzene, 1,3,5-tris (((3',5'-di-tert-butyl-4'-hydroxphenyl) propionyloxyethyl)) isocyanurate, tetrakis ((methylene-β-(3,5-di-tert-butyl-4-hydroxyphenyl) propionate)) methane, 2-tert-butyl-4-methyl-6-(2'-acryloyloxy-3'-tert-butyl-5'-methylbenzyl) phenol, triethylene glycol-bis ((β-(3-tert-butyl-4-hydroxy-5-methylphenyl) propionate)), 3,9-bis (1',1'-dimethyl-2'-hydroxyethyl)-2,4,8,10-tetra-oxaspiro ((5,5)) undecanbis ((β-(3-tert-butyl-4-hydroxy-5-methylphenyl) propionate)).

Another improvement can be realized by adding sulfuric anti-oxidants to the composition by this invention for further oxidative stability. As these sulfuric antioxidants, we may enumerate, for example, such dialkylthiodipropionates as dilauryls, dimyristyls and distearyl esters of thiodipropionates and β-alkylmercaptopropionic acid esters of such polyols as pentaerythritol tetra-(β-dodecyl mercaptoproprionate).

The light and temperature resistance of the composition by this invention may further be improved by adding thereto organic phosphite compounds. Some examples of these phosphorous compounds are: trisnonylphenyl phosphite, tris (2,4-di-tert-butylphenyl) phosphite, tridecyl phosphite, octyldiphenyl phophite, di (tridecyl) pentaerythritol diphosphite, distearyl pentaerythritol diphosphite, di (nonylphenol) pentaerithritol diphosphite, bis (2,4-di-tert-butylphenyl) pentaerithritol diphosphite bis (2,6-di-tert-butyl-4-methylphenyl) pentaerithritol diphosphite, tetra ($C_{12}$-$C_{15}$ alkyl isopropylidene diphenol diphosphite, tetra (tridecyl) 4,4'-n-butylidenebis (2-tert-butyl-5-methylphenol) diphosphite, hexa (tridecyl)-1,1,3-tris (3-(3'-tert-butyl-4'-hydroxy-5'-methyphenyl) butanetriphosphite.

Furthermore the light resistance of the composition by this invention can more improved by adding thereto such light stabilizers as ultraviolet absorbing agents, hindered amine compounds and others.

Some examples of these light stabilizers are: such 2-hydroxybenzophenones as 2,4-dihydroxybenzophenone, 2-hydroxy-4-methoxybenzophenone, 2-hydroxy-4-octoxybenzophenone, 5,5'-methylenebis (2-hydroxy-4-methoxybenzophenone); such 2-(2'-hydroxyphenyl) benzotriazoles as 2-(2'-hydroxy-5'-methylphenyl) benzotriazole, 2-(2'-hydroxy-'5-tert-octylphenyl) benzotriazole, 2-(2'-hydroxy-3',5'-di-tert-butylphenyl) benzotriazole, 2-(2'-hydroxy-3, 5'-di-tert-butylphenyl)-5-chlorobenzotriazole, 2-(2'-hydrozy-3'-tert-butyl-5'-methylphenyl-5-methylphenyl)-5-chlorobenzotriazole, 2-(2'-hydroxy-3',5'-dicumylphenyl) benzotriazol 2,2'-methylenebis (4-tert-octyl-6-benzotriazol) phenol; such benzoates as phenyl salicylate, resorcinol monobenzoate, 2,4-di-tert-butylphenyl-3,5'-di-tertbutyl-4-hydroxybenzoate, hexadecyl-3,5-di-tertbutyl-4-hydroxybenzoate; such substituted oxanhydrides as 2-ethyl-2'-ethoxyoxanhydride, 2-ethoxy-4'-dodecyloxanhydride; such cyanoacrylates as ethyl-α-cyano-β, β-diphenylacrylate, methyl-2-cyano-3-methyl-3-(p-methoxyphenyl) acrylate; such hindered amine compounds as 2,2,6,6-tetramethyl-4-piperidylstearate, 1,2,2,6,6-pentamethyl-4-piperidylstearate, 2,2,6,6-tetramethyl-4-piperidylbenzoate, bis (2,2,6,6-tetramethyl-4-piperidyl) sebacate, bis (1,2,2,6,6-pentamethyl-4-piperidyl) sebacate, tetrakis (2,2,6,6-tetramethyl-4 -piperidyl) butanetetracarboxylate, tetrakis (1,2,2,6,6-pentamethyl-4-piperidyl) 1,2,3,4-butanetetracarboxylate, bis (1,2,2,6,6-pentamethyl-4-piperidyl) di (tridecyl)-1,2,3,4-butanetetracarboxylate, bis (1,2,2,6, 6-pentamethyl-4-piperidyl)-2-butyl-2-(3,5-ditera-butyl-4-hydroxybenzyl) malonate, 1-(2-hydroxyethyl)-2,2,6,6-tetramethyl-4-piperidynol/diethyl succinate polycondensate, 1,6-bis (2,2,6,6-tetramethyl-4-piperidylamino) hexane/dibromoethane polycondensate, 1,6-bis (2,2,6,6-tetramethyl-4-piperidylamino) hexane/2,4-dichlo-6-tert-octylamino-s-triazine polycondensate, 1,6-bis (2,2 6,6-tetramethyl-4-piperidylamino) hexane/2,4-dichloro-6-morpholino-s-triazine polycondensate.

As occasion arises, the composition by this invention may also contain: heavy metal inactivation agents, nucleating agents, metallic soap, pigment, fillers (loading agents), organic tin compounds, plasticizers, epoxides, blowing (foaming) agents, anti-static agents, flame-retardants, lubricants and process aids.

To further illustrate this invention, and not by way of limitation, the following working examples are given:

WORKING EXAMPLE 1

First according to the proportioning as below, pellet was made by extrusion at 280° C. Then it underwent injection molding to be made into test pieces of 1 mm in thickness.

With these test pieces we conducted a thermal stability test in an oven at 160° C. To examine their light resistance they were irradiated by fluorescent lamp for 72 hours and the yellowing factor thereof was measured by Hunter color difference meter.

Further to evaluate their processing safety factor we measured the variation of their melt index with the extrusion once effected at 280° C. and five times repeated (MI(1) and MI(5): g/10 min , 230° C., load 2160 g), whose results are given in Table 2 hereafter.

PROPORTIONING

| | |
|---|---|
| Polypropyrene (Profax 6501) | 100 parts in weight |
| Tetrakis ((methylene-β-(3,5-di-tert-butyl-4-hydroxyphenyl) propionate)) methane | 0.1 part in weight |
| Calcium stearate | 0.05 part in weight |
| Specimen compound | 0.1 part in weight |

TABLE 2

| No. | SPECIMEN COMPOUND | THERMAL STABILITY Hours | YELLOWING FACTOR | MELT INDEX | | |
|---|---|---|---|---|---|---|
| | | | | MI (1) | MI (5) | MI (5)/MI (1) |
| Comparison | | | | | | |
| 2-1 | COMP. COMPOUND A*1 | 288 | 10.7 | 2.1 | 3.0 | 1.43 |
| 2-2 | COMP. COMPOUND B*2 | 276 | 12.9 | 2.2 | 3.3 | 1.50 |
| 2-3 | COMP. COMPOUND C*3 | 312 | 9.8 | 1.9 | 2.5 | 1.32 |
| 2-4 | COMP. COMPOUND D*4 | 288 | 12.1 | 2.1 | 2.9 | 1.38 |
| Working | | | | | | |
| 2-1 | COMPOUND NO. 1 | 348 | 7.5 | 1.7 | 2.0 | 1.18 |
| 2-2 | COMPOUND NO. 2 | 360 | 7.4 | 1.6 | 1.8 | 1.13 |
| 2-3 | COMPOUND NO. 5 | 360 | 7.5 | 1.6 | 1.8 | 1.13 |
| 2-4 | COMPOUND NO. 6 | 348 | 7.7 | 1.8 | 2.1 | 1.17 |
| 2-5 | COMPOUND NO. 9 | 348 | 7.6 | 1.7 | 2.1 | 1.24 |

TABLE 2-continued

| No. | SPECIMEN COMPOUND | THERMAL STABILITY Hours | YELLOWING FACTOR | MELT INDEX | | |
|---|---|---|---|---|---|---|
| | | | | MI (1) | MI (5) | MI (5)/MI (1) |
| 2-6 | COMPOUND NO. 10 | 360 | 7.5 | 1.7 | 2.0 | 1.18 |

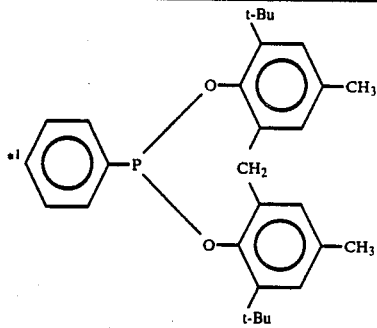

\*1

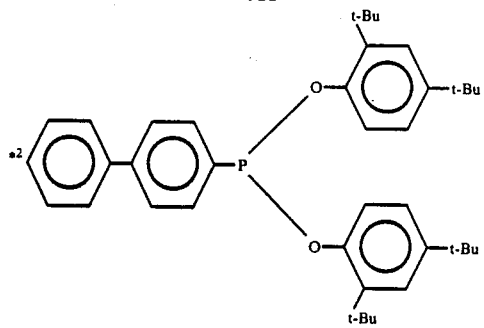

\*2

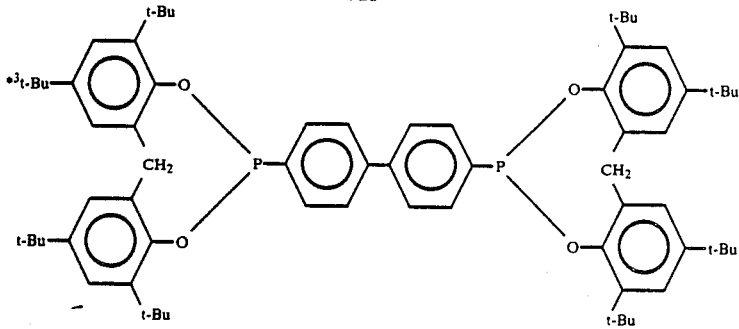

\*3

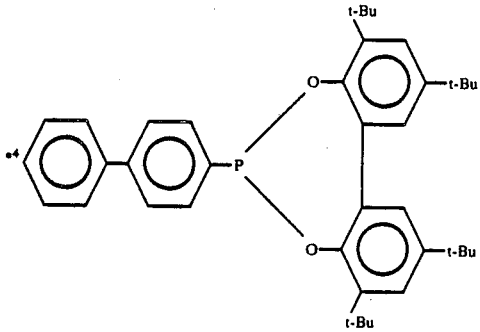

\*4

WORKING EXAMPLE 2

The following compounding ingredients were first extruded at 250° C., then injection molded at 250° C. to be made into test pieces of 1 mm in thickness.

With these test pieces we conducted a thermal stability test in an oven at 160° C., whose results are shown in Table 3.

| | |
|---|---|
| Polypropyrene (Profax 6501) | 100 parts in weight |
| Talc | 20 parts in weight |
| Tetrakis ((methylene ($\beta$-3,5-di-tetra-butyl-4-hydroxyphenyl) propionate)) methane | 0.1 part in weight |
| Calcium stearate | 0.05 part in weight |
| Distearylthiodi-propionate | 0.2 part in weight |
| Specimen compound | 0.1 part in weight |

TABLE 3

| No. | Specimen Compound | Thermal Stability Hours |
|---|---|---|
| Comparison | | |
| 2-1 | NONE | 264 |
| 2-2 | COMP. COMPOUND A | 312 |
| 2-3 | COMP. COMPOUND B | 288 |
| 2-4 | COMP. COMPOUND C | 360 |
| 2-5 | COMP. COMPOUND D | 312 |
| Working | | |
| 2-1 | COMPOUND NO. 2 | 456 |
| 2-2 | COMPOUND No. 3 | 408 |
| 2-3 | COMPOUND No. 4 | 432 |
| 2-4 | COMPOUND NO. 5 | 456 |
| 2-5 | COMPOUND NO. 7 | 432 |
| 2-6 | COMPOUND NO. 8 | 408 |
| 2-7 | COMPOUND NO. 11 | 408 |

WORKING EXAMPLE 3

100 parts in weight of unsaturated linear low density polyethylene, 0.02 part in weight of stearyl-$\beta$-(3,5-di-tert-butyl-4-hydroxyphenyl) propionate and 0.02 part in weight of specimen compounds were put on a Brabender plastograph and blended for 60 minutes under the condition of 230° C.×80 rpm to see the variation with time of the yellowing factor and carbonyl index (CI), whose results are shown in Table 4.

TABLE 4

| No. | SPECIMEN COMPOUND | CI | YELLOWING FACTOR |
|---|---|---|---|
| Comparison | | | |
| 3-1 | NULL | 2.05 | 50.3 |
| 3-2 | COMP. COMPOUND A | 1.80 | 46.4 |
| 3-3 | COMP. COMPOUND B | 1.90 | 47.7 |
| 3-4 | COMP. COMPOUND C | 1.65 | 43.8 |
| 3-5 | COMP. COMPOUND D | 1.85 | 49.5 |
| Working | | | |
| 3-1 | COMPOUND NO. 1 | 1.30 | 37.2 |
| 3-2 | COMPOUND NO. 2 | 1.20 | 34.6 |
| 3-3 | COMPOUND NO. 4 | 1.35 | 36.7 |
| 3-4 | COMPOUND NO. 5 | 1.20 | 35.1 |
| 3-5 | COMPOUND NO. 6 | 1.35 | 37.5 |
| 3-6 | COMPOUND NO. 8 | 1.35 | 37.8 |
| 3-7 | COMPOUND NO. 10 | 1.25 | 35.4 |

WORKING EXAMPLE 4

According to the blending proportioning as below, we extruded these ingredients at 240° C. into pellet, which was then injection molded at 280° C. to be made into test pieces of 1 mm in thickness We then measured their whiteness after reheating for 30 minutes in an oven at 180° C. and the Izod impact strength (kg/cm$^2$) after two weeks' heating in an oven at 120° C. The results are shown in Table 5.

PROPORTIONING

| | |
|---|---|
| Unstabilized ABS resin | 100 parts in weight |
| Calcium stearate | 0.5 part in weight |
| n-octadecyl-$\beta$-(4-hydroxy-3,5-di-tert-butylphenyl) propionate | 0.2 part in weight |
| Specimen compound | 0.3 part in weight |

TABLE 5

| No. | SPECIMEN COMPOUND | IZOD IMPACT STRENGTH | WHITENESS |
|---|---|---|---|
| Comparison | | | |
| 4-1 | NULL | 8.7 | 19.3 |
| 4-2 | COMP. COMPOUND A | 13.6 | 25.7 |
| 4-3 | COMP. COMPOUND B | 13.0 | 24.6 |
| 4-4 | COMP. COMPOUND C | 14.3 | 27.8 |
| 4-5 | COMP. COMPOUND D | 13.2 | 24.9 |
| Working | | | |
| 4-1 | COMPOUND NO. 2 | 16.5 | 32.5 |
| 4-2 | COMPOUND NO. 3 | 15.7 | 30.8 |
| 4-3 | COMPOUND NO. 4 | 15.9 | 31.5 |
| 4-4 | COMPOUND NO. 5 | 16.3 | 32.2 |
| 4-5 | COMPOUND NO. 7 | 16.0 | 30.4 |
| 4-6 | COMPOUND NO. 9 | 15.9 | 31.7 |
| 4-7 | COMPOUND NO. 11 | 15.3 | 30.2 |

WORKING EXAMPLE 5

According to the blending proportion as below, the ingredients were extruded at 280° C. to be made into pellet. After holding the pellet at 280° C. for 5 minutes, it was injection molded into test pieces of 12.7 mm in thickness. With these test pieces, we conducted measurements of Izod impact strength and whiteness. The results are shown in Table 6.

PROPORTIONING

| | |
|---|---|
| Polycarbonate resin | 50 parts in weight |
| Heat resistant ABS resin ($\alpha$-methylstyrene content: 40%) | 50 parts in weight |
| 1,3,5-tris(4-hydroxy-3,5-di-tert-butylbenzyl) isocyanurate | 0.3 part in weight |
| Specimen compound | 0.3 part in weight |

TABLE 6

| No. | SPECIMEN COMPOUND | IZOD IMPACT STRENGTH | WHITENESS |
|---|---|---|---|
| Comparison | | | |
| 5-1 | NULL | 1.0 | 27.3 |
| 5-2 | COMP. COMPOUND A | 1.2 | 26.5 |
| 5-3 | COMP. COMPOUND B | 1.1 | 26.0 |
| 5-4 | COMP. COMPOUND C | 1.4 | 29.4 |
| 5-5 | COMP. COMPOUND D | 1.2 | 26.2 |
| Working | | | |
| 5-1 | COMPOUND NO. 1 | 1.9 | 34.6 |
| 5-2 | COMPOUND No. 2 | 2.1 | 35.7 |
| 5-3 | COMPOUND NO. 3 | 1.8 | 32.9 |
| 5-4 | COMPOUND NO. 5 | 2.0 | 35.5 |
| 5-5 | COMPOUND NO. 7 | 1.8 | 32.6 |
| 5-6 | COMPOUND No. 9 | 2.0 | 33.4 |
| 5-7 | COMPOUND NO. 10 | 1.9 | 34.2 |

WORKING EXAMPLE 6

45 parts in weight of polyphenylene oxide resin, 55 parts in weight of shock-resistant polystyrene resin, 0.25 part in weight of 1,3,5-tris (4-hydroxy-3,5-di-tert-butylbenzyl) isocyanurate and 0.5 part in weight of specimen compound were belended. After extruded at 280° C., they were injection molded at 280° C. to be made into test pieces. With these test pieces we conducted measurement of their Izod impact strength after two weeks' reheating at 120° C.

The results are shown in Table 7.

TABLE 7

| Specimen No. | Compound | IZOD IMPACT STRENGTH | |
|---|---|---|---|
| | | BEFORE HEATING | AFTER HEATING |
| Comparison | | | |
| 6-1 | COMP. COMPOUND A | 11.5 | 6.4 |
| 6-2 | COMP. COMPOUND B | 10.9 | 5.8 |
| 6-3 | COMP. COMPOUND C | 12.0 | 7.6 |
| 6-4 | COMP. COMPOUND D | 11.2 | 6.3 |
| Working | | | |
| 6-1 | COMPOUND NO. 1 | 12.6 | 10.5 |
| 6-2 | COMPOUND NO. 2 | 12.8 | 10.9 |
| 6-3 | COMPOUND NO. 5 | 12.5 | 10.1 |
| 6-4 | COMPOUND NO. 6 | 12.3 | 9.8 |
| 6-5 | COMPOUND NO. 8 | 12.5 | 10.3 |
| 6-6 | COMPOUND NO. 10 | 12.3 | 10.1 |
| 6-7 | COMPOUND NO. 11 | 12.2 | 10.0 |

What is claimed is:

1. A synthetic resin composition comprises 100 parts by weight of a synthetic resin, 0.01 to 10 parts by weight of a cyclic phosphonite compound having the following formula (I):

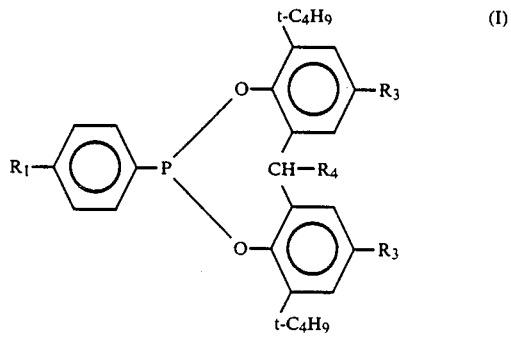

in which $R_1$ is an alkyl, phenyl or an alkylphenyl, $R_3$ is an alkyl, $R_4$ is hydrogen or methyl, and 0.001 to 5 parts by weight of an anti-oxidant of an ester of a 3,5-dialkyl-4-hydroxyphenyl-propionic acid or a tris(alkylated-hydroxybenzyl)isocyanurate.

2. The composition as claimed in claim 1, in which the anti-oxidant comprises 3,5-dialkyl-4-hydroxyphenylpropionic acid ester.

3. The composition as claimed in claim 1, in which the anti-oxidant comprises tetrakis(methylene-beta-(3,5-di-tertiary-butyl-4-hydroxyphenyl)propionate)methane.

4. The composition as claimed in claim 1, in which the anti-oxidant comprises stearyl-beta-(3,5-di-tertiary-butyl-4-hydroxyphenyl)propionate.

5. The composition as claimed in claim 1, in which the anti-oxidant comprises tris(alkylated-hydroxybenzyl)-isocyanurate.

6. The composition as claimed in claim 1, in which the anti-oxidant comprises 1,3,5-tris(3,5-di-tertiary-4-hydroxybenzyl)isocyanurate.

7. The composition as claimed in claim 1, in which the resin comprises a polyolefin.

8. The composition as claimed in claim 1, in which $R_1$ comprises an alkyl having 1 to 18 carbon atoms, $R_3$ is an alkyl having 1 to 18 carbon atoms.

9. The composition as claimed in claim 1, in which $R_1$ is methyl, $R_3$ is an alkyl having 1 to 4 carbon atoms and $R_4$ is hydrogen.

10. The composition as claimed in claim 1, in which $R_1$ is phenyl.

* * * * *